US008383276B2

(12) United States Patent
Muldoon et al.

(10) Patent No.: US 8,383,276 B2
(45) Date of Patent: Feb. 26, 2013

(54) HIGH VOLTAGE ELECTROLYTE

(75) Inventors: John Muldoon, Saline, MI (US); Gary Allred, Wake Forest, NC (US); Anthony Dotse, Cary, NC (US)

(73) Assignees: Toyota Motor Engineering & Manufacturing North America, Inc., Erlanger, KY (US); Synthonix Corporation, Wake Forest, NC (US)

( * ) Notice: Subject to any disclaimer, the term of this patent is extended or adjusted under 35 U.S.C. 154(b) by 400 days.

(21) Appl. No.: 12/822,444

(22) Filed: Jun. 24, 2010

(65) Prior Publication Data

US 2011/0008680 A1 Jan. 13, 2011

Related U.S. Application Data

(60) Provisional application No. 61/219,996, filed on Jun. 24, 2009.

(51) Int. Cl.
*H01M 6/16* (2006.01)

(52) U.S. Cl. ........ 429/339; 429/326; 429/330; 429/340; 429/341; 429/342; 429/199; 429/307; 252/62.2; 564/98

(58) Field of Classification Search .................. 429/339, 429/326, 330, 340, 341, 342, 199, 307; 252/62.2; 564/98
See application file for complete search history.

(56) References Cited

U.S. PATENT DOCUMENTS

| 2005/0118512 A1 | 6/2005 | Onuki et al. |
| 2007/0238025 A1 | 10/2007 | Onuki et al. |

FOREIGN PATENT DOCUMENTS

| JP | 11-067265 A | 3/1999 |
| JP | 2002-110225 A | 4/2002 |
| KR | 10-2007-0045975 | 5/2007 |

OTHER PUBLICATIONS

Brink et al. "IR and Raman spectra of methylsulfonylhydroxylamines", Spectrochimica Acta, Part A: Molecular and Biomolecular Spectroscopy (1986), 42A (4), pp. 525-529.*
International Search Report; International Application No. PCT/US2010/039781; search report dated Jan. 28, 2011.

* cited by examiner

*Primary Examiner* — Laura Weiner
(74) *Attorney, Agent, or Firm* — Gifford, Krass, Sprinkle, Anderson & Citkowski, P.C.

(57) ABSTRACT

An organic electrolyte solvent includes a compound of the formula: $R_1$—$SO_2$—$NR_2$—$OR_3$ wherein $R_1$ is selected from alkanes, alkenes, alkynes, aryls and their substituted derivatives and perfluorinated analogues; $R_2$ is selected from alkanes, alkenes, alkynes, aryls and their substituted derivatives; $R_3$ is selected from alkanes, alkenes, alkynes, aryls and their substituted derivatives wherein the electrolyte solvent is stable at voltages of greater than 4.0 volts.

26 Claims, No Drawings

HIGH VOLTAGE ELECTROLYTE

CROSS-REFERENCE TO RELATED APPLICATIONS

This application claims priority of U.S. Provisional Patent Application Ser. No. 61/219,996 filed Jun. 24, 2009, which is incorporated herein by reference.

FIELD OF THE INVENTION

The invention relates to organic electrolyte solvents, organic electrolytic solutions utilizing the organic electrolyte solvents, and batteries utilizing the electrolytic solutions.

BACKGROUND OF THE INVENTION

It is generally known in the art to utilize various organic solvents as electrolytes for chargeable lithium type batteries. Various electrolytes include materials such as carbonates and cyclic esters as well as ethers. However, these conventional organic solvents are prone to decomposition during the cycling of a charge and discharge of a battery.

Additionally, conventional organic solvent type electrolytes are prone to failure at high operating voltages such as greater than 4.0 volts. Such electrolytes may also be prone to thermal failure at elevated temperatures. Failures may result in reduced cycle life and decreased safety of batteries using such electrolytes. There is therefore a need in the art for an improved electrolytic solution that is stable at high voltages and at elevated temperatures. There is also a need in the art for an improved electrolytic solution that improves the cycle life and safety of a battery incorporating the electrolytic solution.

SUMMARY OF THE INVENTION

In one aspect there is disclosed an organic electrolyte solvent that includes a compound of the formula: $R_1$—$SO_2$—$NR_2$—$OR_3$ wherein $R_1$ is selected from alkanes, alkenes, alkynes, aryls and their substituted derivatives and perfluorinated analogues; $R_2$ is selected from alkanes, alkenes, alkynes, aryls and their substituted derivatives; $R_3$ is selected from alkanes, alkenes, alkynes, aryls and their substituted derivatives wherein the electrolyte solvent is stable at voltages of greater than 4.0 volts.

In one aspect there is disclosed an organic electrolyte solvent that includes a compound of the formula: $R_1O$—$SO_2$—$NR_2$—$OR_3$ wherein $R_1$ is selected from alkanes, alkenes, alkynes, aryls and their substituted derivatives and perfluorinated analogues; $R_2$ is selected from alkanes, alkenes, alkynes, aryls and their substituted derivatives; $R_3$ is selected from alkanes, alkenes, alkynes, aryls and their substituted derivatives wherein the electrolyte solvent is stable at voltages of greater than 4.0 volts.

In another aspect there is disclosed an organic electrolytic solution that includes an organic electrolyte solvent that includes a compound of the formula: $R_1$—$SO_2$—$NR_2$—$OR_3$ wherein $R_1$ is selected from alkanes, alkenes, alkynes, aryls and their substituted derivatives and perfluorinated analogues; $R_2$ is selected from alkanes, alkenes, alkynes, aryls and their substituted derivatives; $R_3$ is selected from alkanes, alkenes, alkynes, aryls and their substituted derivatives wherein the electrolytic solution is stable at voltages of greater than 4.0 volts.

In another aspect there is disclosed an organic electrolytic solution that includes an organic electrolyte solvent that includes a compound of the formula: $R_1O$—$SO_2$—$NR_2$—$OR_3$ wherein $R_1$ is selected from alkanes, alkenes, alkynes, aryls and their substituted derivatives and perfluorinated analogues; $R_2$ is selected from alkanes, alkenes, alkynes, aryls and their substituted derivatives; $R_3$ is selected from alkanes, alkenes, alkynes, aryls and their substituted derivatives wherein the electrolytic solution is stable at voltages of greater than 4.0 volts.

In a further aspect there is disclosed a battery that includes a cathode, anode and electrolytic solution that includes an organic electrolyte solvent including a compound of the formula: $R_1$—$SO_2$—$NR_2$—$OR_3$ wherein $R_1$ is selected from alkanes, alkenes, alkynes, aryls and their substituted derivatives and perfluorinated analogues; $R_2$ is selected from alkanes, alkenes, alkynes, aryls and their substituted derivatives; $R_3$ is selected from alkanes, alkenes, alkynes, aryls and their substituted derivatives wherein the electrolytic solution is stable at voltages of greater than 4.0 volts.

In a further aspect there is disclosed a battery that includes a cathode, anode and electrolytic solution that includes an organic electrolyte solvent including a compound of the formula: $R_1O$—$SO_2$—$NR_2$—$OR_3$ wherein $R_1$ is selected from alkanes, alkenes, alkynes, aryls and their substituted derivatives and perfluorinated analogues; $R_2$ is selected from alkanes, alkenes, alkynes, aryls and their substituted derivatives; $R_3$ is selected from alkanes, alkenes, alkynes, aryls and their substituted derivatives wherein the electrolytic solution is stable at voltages of greater than 4.0 volts.

DETAILED DESCRIPTION OF THE PREFERRED EMBODIMENTS

In one aspect there is disclosed an organic electrolyte solvent that includes a compound of the formula: $R_1$—$SO_2$—$NR_2$—$OR_3$ or: $R_1O$—$SO_2$—$NR_2$—$OR_3$ wherein $R_1$ is selected from alkanes, alkenes, alkynes, aryls and their substituted derivatives and perfluorinated analogues; $R_2$ is selected from alkanes, alkenes, alkynes, aryls and their substituted derivatives; $R_3$ is selected from alkanes, alkenes, alkynes, aryls and their substituted derivatives. The organic electrolyte solvent remains stable at voltages of greater than 4.0 volts. In another aspect, $R_1$, $R_2$ and $R_3$ may be selected from linear alkyl, branched alkyl, partially fluorinated alkyl and fully fluorinated alkyl groups having from 1 to 5 carbons. In a preferred aspect, $R_2$ and $R_3$ may include a methyl moiety.

In another aspect, there is disclosed an organic electrolytic solution that includes the organic electrolyte solvent that includes a compound of the formula: $R_1$—$SO_2$—$NR_2$—$OR_3$ or: $R_1O$—$SO_2$—$NR_2$—$OR_3$ wherein $R_1$ is selected from alkanes, alkenes, alkynes, aryls and their substituted derivatives and perfluorinated analogues; $R_2$ is selected from alkanes, alkenes, alkynes, aryls and their substituted derivatives; $R_3$ is selected from alkanes, alkenes, alkynes, aryls and their substituted derivatives. Additionally, an electrolyte salt may be dissolved in the organic electrolyte wherein the electrolytic solution remains stable at voltages of greater than 4.0 volts. The perfluorinated analogues may be synthesized by electrochemical fluorination (ECF) or direct fluorination of a desired substrate.

Various electrolyte salts may include lithium salts that are generally used in the field. In one aspect, lithium salts may be selected from the group consisting of: $LiPF_6$, $LiAsF_6$, $LiSbF_6$, $LiBF_4$, $LiClO_4$, $LiCF_3SO_3$, $Li(CF_3SO_2)_2N$, $Li(C_2F_5SO_2)_2N$, $LiC_4F_9SO_3$, $Li(CF_3SO_2)_3C$, $LiBPh_4$, LiBOB, and $Li(CF_3SO_2)(CF_3CO)N$ and combinations thereof. The organic electrolyte solution may include the electrolyte salts in a concentration of from 0.5 molar to 3 molar.

The organic electrolyte solution may also include electrolyte additives selected from solid electrolyte interface (SEI) forming additives, cathode protecting agents, salt stabilizers, overcharge protecting additives, lithium depositing additives, salvation enhancers, as well as corrosion inhibitors and wetting agents.

In one aspect, the SEI forming additives may be utilized to improve the formation of an SEI layer on the surface of an anode of a battery, as will be discussed in more detail below. In one aspect, the SEI forming additives may be selected from the group consisting of: vinylene carbonate, vinyl ethylene carbonate, ethylene carbonate, allyl ethyl carbonate, vinyl acetate, divinyl adipate, acrylic acid nitrile, 2-vinyl pyridine, maleic anhydride, maleimides, methyl cinnamate, phosphonate, vinyl-containing silane-based compounds, furan derivatives that contain two double bonds in each molecule, sulfur-based compounds, including $SO_2$, polysulfide, cyclic alkyl sulfites, aryl sulfites, nitrates, nitrites, halogenated ethylene carbonate, halogenated lactone, methyl chloroformate, carboxyl phenol, aromatic esters, anhydrides, succinimide, N-benzyloxy carbonyloxy succinimide, aromatic isocyanates, $B_2O_3$, organic borates, boroxine compounds, lithium salt-based boron compounds, halogenated organic compounds, polydimethylsiloxane, silanes, tris(pentafluorophenyl) borane, and alkali metal salts.

The cathode protecting agents may also be included in the organic electrolyte solution. The cathode protecting agents may be selected from the group consisting of: amine-based organic bases such as butylamine, carbodiimide based compounds such as N,N-dicyclohexylcarbodiimide, N,N-diethylamino trimethylsilane.

Various salt stabilizers may be utilized in the organic electrolyte solution and may be selected from the group consisting of: LiF, Lewis bases including tris(2,2,2-trifluoroethyl) phosphate, amide-based compounds including 1-methyl-2-pyrrolidinone, fluorinated carbamate and hexamethyl-phosphoramide.

Additionally, overcharge protecting additives may be included in the organic electrolyte solution. In one aspect, the overcharge protecting additives may be selected from the group consisting of metallocenes, tetracyanoethylene, tetramethylphenylenediamine, dihydrophenazine derivatives bearing either 2-hydroxypropyl or ethyl substituents on both N atoms, substituted aromatic or heterocyclic compounds and their alkali metal salts, anisole-family compounds, 2,5-diter-tbutyl-1,4-dimethoxybenzene, monomethoxy benzene class compounds, hexaethyl benzene, bipyridyl or biphenyl carbonates, difluoroanisoles, S- or N-containing heterocyclic aromatic compounds such as thianthrene and 2,7-diacetyl thianthrene, phenothiazinebased compounds, lithium fluorododecaborates, xylene, cyclohexylbenzene, biphenyl, 2,2-diphenylpropane, phenyl-tert-butyl carbonate, phenyl-R-phenyl compounds, 3-thiopheneacetonitrile, heterocyclic compounds including furan, thiophene, and N-methylpyrrole, 3,4-ethylenedioxythiophene, and LiBOB.

Various lithium depositing additives may also be included in the organic electrolyte solution. The lithium depositing additives may be selected from the group consisting of: $SO_2$ compounds, polysulfide, water, 2-methyltetrahydrofuran, 2-methylthiophene, nitromethane, tetraalkylammonium chlorides with a long alkyl chain, cetyltrimethylammonium chlorides, lithium and tetraethylammonium salts of perfluorooctanesulfonate, perfluoropolyethers, nitrile sucrose, nitrile cellulose, $AlI_3$, SnI, HF, and fluoroethylene carbonate.

Salvation enhancers may also be included in the organic electrolyte solution. Various salvation enhancers include borates, boranes and borole compounds.

In addition, corrosion inhibitors and wetting agents may also be included in the organic electrolyte solution. Various corrosion inhibitors and wetting agents may include agents selected from the group consisting of: LiBOB, LiODFB, ionic and non-ionic surfactants, cyclohexane, trialkyl phosphate, linear esters with high molecular weight including methyl decanoate and dodecyl acetate, tertiary carboxylic acids, and $P_2O_5$.

Additionally, other solvents may be included in the organic electrolyte solution. The additional solvents may include organic carbonates, ionic liquids, silanes and sulfones.

In another aspect, a lithium battery that includes the organic electrolytic solution is described. Generally, the battery may include a positive and negative electrode as well as a separator material and the organic electrolytic solution. Various types of batteries including lithium batteries such as lithium secondary batteries, lithium ion batteries and lithium ion polymer batteries as well as lithium primary batteries may utilize the organic electrolytic solution.

In one aspect, the cathode may include an active material for which absorption and release of various cations of the lithium salts can take place. In one aspect, the active material may include the cations. For example, in a battery that is charged and discharged through the migration of lithium ions such as a lithium ion secondary battery, various lithium composite oxides containing lithium and a transition metal may be utilized. Various examples include composite oxides with the general formula $LiMO_2$ where M can be any metallic elements or combination of metallic elements such as cobalt, aluminum, chromium, manganese, nickel, iron, vanadium, magnesium, titanium, zirconium, niobium, molybdenum, copper, zinc, indium, strontium, lanthanum, and cesium. Additionally, the active material can be made of a material with the chemical formula $LiMn_2O_4$ or a material with the general formula $LiMPO_4$ where M can be any metallic element or combination of elements such as cobalt, aluminum, chromium, manganese, nickel, iron, vanadium, magnesium, titanium, zirconium, niobium, molybdenum, copper, zinc, indium, strontium, lanthanum, and cesium The positive electrode of the battery disclosed may include any of the active materials that may be held on an electrically conductive member that includes metal or another conductive element. Various conductive members including rod-shaped, plate or foil bodies as well as mesh or other type structures. In addition to the active material and electron conducting material various other materials such as binders may also be included. Various binders including polyvinylidene fluoride, polyvinyl diamine fluoride, polytetrafluoroethylene, polyvinyl diamine fluoride, hexafluoropropylene copolymers, styrene butadiene rubber and various other materials may be utilized.

The negative electrode or anode may also include an active material for which absorption and release of the cation described above can take place. Various negative electrode active materials may include a carbon material having an amorphous structure and/or graphite structure. For example, various kinds of active materials commonly utilized in lithium batteries may include natural graphite, mezocarbon microbeads, highly ordered pyrolytic graphite, hard carbon and soft carbon, as well as additional materials. Further, various other active materials that are able to maintain the electric potential of the negative electrode such as lithium titanate may also be utilized. Additionally, elements that can alloy with lithium such as tin, silicon, antimony, bismuth, silver, zinc, aluminum, lead, germanium, arsenic and composite materials containing said elements can be utilized as negative electrode active materials. As with the positive electrode, the negative electrode may include an active material that is held on an electrically conductive member that includes metal or the like. Various structures including plates, rods, foils and other type structures may be utilized. As with the previously described cathode, a binder material may be mixed with the active material as well as other additives such as plasticizers or other such additives to form the negative electrode of the battery.

The battery also includes the electrolytic solution as described above. The electrolytic solution may include an organic electrolyte solvent including a compound of the formula: $R_1$—$SO_2$—$NR_2$—$OR_3$ or $R_1O$—$SO_2$—$NR_2$—$OR_3$ wherein $R_1$ is selected from alkanes, alkenes, alkynes, aryls and their substituted derivatives and perfluorinated analogues; $R_2$ is selected from alkanes, alkenes, alkynes, aryls and their substituted derivatives; $R_3$ is selected from alkanes, alkenes, alkynes, aryls and their substituted derivatives, and an electrolyte salt dissolved in the organic electrolyte wherein the battery is stable at voltages of greater than 4.0 volts.

EXAMPLES

Preparation of
N-methoxy-N-methyl-methanesulfonamide

To a 3-neck 1.0-L round-bottomed flask (RBF) equipped with dry ice/liquid nitrogen bath, mechanical stirrer, dry nitrogen gas inlet, thermoprobe, addition funnel, and bubbler were charged with methanesulfonyl chloride (25 g, 0.218 M), N,O-dimethylhydroxylamine hydrochloride (22.35 g 0.229 M) and anhydrous dichloromethane (200 mL). The system was flushed with nitrogen and then cooled to 0° C. While stirring at this temperature, anhydrous trimethylamine (3.00 equivalents) was added dropwise and the resulting reaction mixture was stirred and allowed to warm up to room temperature and stirred overnight. The reaction mixture was cooled to 0° C. and filtered to remove the solid (triethylamine hydrochloride) and the solvent was removed on a rotary evaporator. The reaction mixture may be purified though a short pad of celite and eluted with ether, with subsequent removal of the ether. The reaction product may be pulled under high vacuum overnight to yield a pure product.

Although preferred embodiments of the invention have been described using specific terms, devices, and methods, such description is for illustrative purposes only. The words used are words of description rather than of limitation. It is to be understood that changes and variations may be made by those of ordinary skill in the art without departing from the spirit or the scope of the present invention which is set forth in the following claims. In addition, it should be understood that aspects of the various embodiments may be interchanged, both in whole, or in part. Therefore, the spirit and scope of the appended claims should not be limited to the description of the preferred versions contained therein.

The invention claimed is:
1. An organic electrolytic solution comprising:
an organic electrolyte solvent including a compound of the formula:

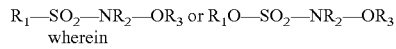
wherein $R_1$ is selected from alkanes, alkenes, alkynes, aryls and their substituted derivatives and perfluorinated analogues; $R_2$ is selected from alkanes, alkenes, alkynes, aryls and their substituted derivatives; $R_3$ is selected from alkanes, alkenes, alkynes, aryls and their substituted derivatives; and an electrolyte salt dissolved in the organic electrolyte solvent wherein the electrolytic solution is stable at voltages of greater than 4.0 volts.

2. The organic electrolytic solution of claim 1 including additional solvents selected from organic carbonates, ionic liquids, silanes and sulfones.

3. The organic electrolytic solution of claim 1 wherein $R_1$ is a perfluorinated analogue synthesized by electrochemical fluorination.

4. The organic electrolytic solution of claim 1 wherein R1 is perfluorinated analogue synthesized by direct fluorination.

5. The organic electrolytic solution of claim 1 wherein the electrolyte salt is selected from the group consisting of: $LiPF_6$, $LiAsF_6$, $LiSbF_6$, $LiBF_4$, $LiClO_4$, $LiCF_3SO_3$, $Li(CF_3SO_2)_2N$, $Li(C_2F_5SO_2)_2N$, $LiC_4F_9SO_3$, $Li(CF_3SO_2)_3C$, $LiBPh_4$, LiBOB, and $Li(CF_3SO_2)(CF_3CO)N$ and combinations thereof.

6. The organic electrolytic solution of claim 5 wherein the electrolyte salt has a concentration of from 0.5M to 3.0M.

7. The organic electrolytic solution of claim 1 including electrolyte additives selected from the group consisting of SEI forming additives, cathode protecting agents, salt stabilizers, overcharge protecting additives, lithium depositing additives, and salvation enhancers, corrosion inhibitors and wetting agents.

8. The organic electrolyte solution of claim 7 wherein the SEI forming additives are selected from the group consisting of: vinylene carbonate, vinyl ethylene carbonate, ethylene carbonate, allyl ethyl carbonate, vinyl acetate, divinyl adipate, acrylic acid nitrile, 2 -vinyl pyridine, maleic anhydride, maleimides, methyl cinnamate, phosphonate, vinyl-containing silane-based compounds, furan derivatives that contain two double bonds in each molecule, sulfur-based compounds, including $SO_2$, polysulfide, cyclic alkyl sulfites, aryl sulfites, nitrates, nitrites, halogenated ethylene carbonate, halogenated lactone, methyl chloroformate, carboxyl phenol, aromatic esters, anhydrides, succinimide, N-benzyloxy carbonyloxy succinimide, aromatic isocyanates, $B_2O_3$, organic borates, boroxine compounds, lithium salt-based boron compounds, halogenated organic compounds, polydimethylsiloxane, silanes, tris(pentafluorophenyl)borane, and alkali metal salts.

9. The organic electrolyte solution of claim 7 wherein the cathode protecting agents are selected from the group consisting of: amine-based organic bases such as butylamine, carbodiimide based compounds such as N,N-dicyclohexylcarbodiimide, N,N-diethylamino trimethylsilane.

10. The organic electrolyte solution of claim 7 wherein the salt stabilizers are selected from the group consisting of: LiF, Lewis bases including tris(2,2,2 -trifluoroethyl) phosphate, amide-based compounds including 1-methyl-2-pyrrolidinone, fluorinated carbamate and hexamethyl-phosphoramide.

11. The organic electrolyte solution of claim 7 wherein the overcharge protecting additives are selected from the group consisting of: metallocenes, tetracyanoethylene, tetramethylphenylenediamine, dihydrophenazine derivatives bearing either 2-hydroxypropyl or ethyl substituents on both N atoms, substituted aromatic or heterocyclic compounds and their alkali metal salts, anisole-family compounds, 2,5-ditertbutyl-1,4-dimethoxybenzene, monomethoxy benzene class compounds, hexaethyl benzene, bipyridyl or biphenyl carbonates, difluoroanisoles, S- or N-containing hertocyclic aromatic compounds such as thianthrene and 2,7-diacetyl thianthrene, phenothiazinebased compounds, lithium fluorododecaborates, xylene, cyclohexylbenzene, biphenyl, 2,2-diphenylpropane, phenyl-tert-butyl carbonate, phenyl-R-phenyl compounds, 3-thiopheneacetonitrile, heterocyclic compounds including furan, thiophene, and N-methylpyrrole, 3,4-ethylenedioxythiophene, and LiBOB.

12. The organic electrolyte solution of claim 7 wherein the lithium depositing additives are selected from the group consisting of: $SO_2$ compounds, polysulfide, water, 2-methyltetrahydrofuran, 2-methylthiophene, nitromethane, tetraalkylammonium chlorides with a long alkyl chain, cetyltrimethylammonium chlorides, lithium and tetraethylammonium salts of perfluorooctanesulfonate, perfluoropolyethers, nitrile sucrose, nitrile cellulose, $AlI_3$, SnI, HF, and fluoroethylene carbonate.

13. The organic electrolyte solution of claim 7 wherein the salvation enhancers are selected from the group consisting of: as borate, borane, and borole compounds.

14. The organic electrolyte solution of claim 7 wherein the corrosion inhibitors and wetting agents are selected from the group consisting of: LiBOB, LiODFB, ionic and non-ionic surfactants, cyclohexane, trialkyl phosphate, linear eaters with high molecular weight including methyl decanoate and dodecyl acetate, tertiary carboxylic acids, and $P_2O_5$.

15. A battery comprising:
a cathode;
an anode;
an organic electrolyte solvent including a compound of the formula:

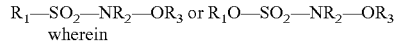
wherein $R_1$ is selected from alkanes, alkenes, alkynes, aryls and their substituted derivatives and perfluorinated analogues; $R_2$ is selected from alkanes, alkenes, alkynes, aryls and their substituted derivatives; $R_3$ is selected from alkanes, alkenes, alkynes, aryls and their substituted derivatives; and an electrolyte salt dissolved in the organic electrolyte wherein the battery is stable at voltages of greater than 4.0 volts.

16. The battery of claim 15 including additional solvents selected from organic carbonates, ionic liquids, silanes and sulfones.

17. The battery of claim 15 wherein $R_1$ is a perfluorinated analogue synthesized by electrochemical fluorination.

18. The battery of claim 15 wherein R1 is a perfluorinated analogue synthesized by direct fluorination.

19. The battery of claim 15 wherein the electrolyte salt is selected from the group consisting of: $LiPF_6$, $LiAsF_6$, $LiSbF_6$, $LiBF_4$, $LiClO_4$, $LiCF_3SO_3$, $Li(CF_3SO_2)_2N$, $Li(C_2F_5SO_2)_2N$, $LiC_4F_9SO_3$, $Li(CF_3SO_2)_3C$, $LiBPh_4$, LiBOB, and $Li(CF_3SO_2)(CF_3CO)N$ and combinations thereof.

20. The battery of claim 15 wherein the electrolyte salt has a concentration of from 0.5M to 3.0M.

21. The battery of claim 15 including electrolyte additives selected from the group consisting of: SEI forming additives, cathode protecting agents, salt stabilizers, overcharge protecting additives, lithium depositing additives, and salvation enhancers, corrosion inhibitors and wetting agents.

22. The battery of claim 15 wherein $R_1$, $R_2$ and $R_3$ are selected from linear alkyl, branched alkyl, partially fluorinated alkyl, fully fluorinated allyl groups having from 1 to 5 carbons.

23. An organic electrolyte solvent comprising:
a compound of the formula:

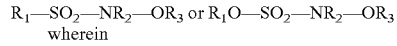

$R_1$ is selected from alkanes, alkenes, alkynes, aryls and their substituted derivatives and perfluorinated analogues; $R_2$ is selected from alkanes, alkenes, alkynes, aryls and their substituted derivatives; $R_3$ is selected from alkanes, alkenes, alkynes, aryls and their substituted derivatives wherein the electrolyte is stable at voltages of greater than 4.0 volts.

24. The organic electrolyte solvent of claim 23 wherein $R_1$, $R_2$ and $R_3$ are selected from linear alkyl, branched alkyl, partially fluorinated alkyl, fully fluorinated alkyl groups having from 1 to 5 carbons.

25. The organic electrolyte solvent of claim 23 wherein $R_2$ comprises a methyl moiety.

26. The organic electrolyte solvent of claim 23 wherein $R_3$ comprises a methyl moiety.

* * * * *